United States Patent [19]
Brunson et al.

[11] Patent Number: 5,724,964
[45] Date of Patent: *Mar. 10, 1998

[54] DISPOSABLE FACE MASK WITH ENHANCED FLUID BARRIER

[75] Inventors: Kevin K. Brunson, Argyle; Frank D. Rasberry, Bedford; Albert R. Rich, Jr., Watauga, all of Tex.

[73] Assignee: Tecnol Medical Products, Inc., Fort Worth, Tex.

[*] Notice: The term of this patent shall not extend beyond the expiration date of Pat. No. 5,322,061.

[21] Appl. No.: 499,063

[22] Filed: Jul. 6, 1995

Related U.S. Application Data

[63] Continuation-in-part of Ser. No. 168,090, Dec. 15, 1993, abandoned, which is a continuation-in-part of Ser. No. 278,930, Jul. 20, 1994, Pat. No. 5,553,608.

[51] Int. Cl.⁶ ..................................................... A62B 7/10
[52] U.S. Cl. .............................. 128/206.19; 128/206.12; 128/206.22; 128/206.25; 128/205.27
[58] Field of Search ........................ 128/206.21, 206.22, 128/206.23, 206.24, 206.25, 206.27, 206.28, 207.11, 205.25, 205.27, 205.29, 206.12, 206.14, 206.18, 206.19; 604/317, 384

[56] References Cited

U.S. PATENT DOCUMENTS

| D. 249,072 | 8/1978 | Revoir | D29/8 |
|---|---|---|---|
| D. 285,733 | 9/1986 | Cooper | D29/8 |
| D. 319,111 | 8/1991 | Sandel | D29/9 |
| D. 327,141 | 6/1992 | Hubbard et al. | D29/9 |
| 1,987,922 | 1/1935 | Blatt | 128/139 |
| 2,012,505 | 8/1935 | Goldsmith | 128/146 |
| 2,116,241 | 5/1938 | Heuman | 128/139 |
| 2,227,667 | 1/1941 | Panettiere | 128/139 |
| 2,248,477 | 7/1941 | Lombard | 128/202 |
| 2,462,005 | 2/1949 | Schauweker | 128/146 |
| 2,494,406 | 1/1950 | Reitano | 128/146 |

(List continued on next page.)

FOREIGN PATENT DOCUMENTS

| 5033179 | 3/1979 | Australia | A62B 7/10 |
|---|---|---|---|
| 1085259 | 8/1978 | Canada . | |
| 0355444 | 7/1989 | European Pat. Off. | A41D 13/00 |
| 0391726 | 10/1990 | European Pat. Off. | B01D 39/14 |
| 0515986 | 12/1992 | European Pat. Off. | A41D 13/00 |
| 0606686 | 1/1994 | European Pat. Off. | A41D 13/00 |
| 3250336 | 5/1994 | European Pat. Off. . | |

(List continued on next page.)

OTHER PUBLICATIONS

Racal Health & Safety brochure, DELTA Disposable Respirators, 1993.

The Mask Collection by Tecnol, Reprinted from *AORN Journal*, 1987.

R1050 AO Safety Products brochure, Dust Demon Foldable, Reusable/Disposable Respirator, 1989.

Glendale brochure, Dustbuster Comfort plus Full Dust and Mist Protection, 1992.

Tecnol Fluidshield brochure, "The Only Masks with Loncet Breathable Film . . . Your Extra Layer of Protection from Body Fluids", 1992.

(List continued on next page.)

*Primary Examiner*—Vincent Millin
*Assistant Examiner*—V. Srivastava
*Attorney, Agent, or Firm*—Baker & Botts, L.L.P.

[57] ABSTRACT

A disposable face mask that includes a filter body capable of filtering liquids and/or particles of a size appropriate for the mask's intended purposes, while providing excellent breathability and comfort to the wearer for extended periods of time. The filter body is formed from multiple layers of filtration material having various configurations. Such masks may be secured by one or more knitted headbands to the head of a wearer. Various gasket-type sealing materials such as plastic film or other materials such as hydrogel may be used to enhance the fluid barrier formed between the periphery of the mask and the wearer's face.

27 Claims, 4 Drawing Sheets

U.S. PATENT DOCUMENTS

| | | | |
|---|---|---|---|
| 2,556,589 | 6/1951 | Le Duc | 128/146 |
| 2,762,368 | 9/1956 | Bloomfield | 128/146 |
| 2,921,581 | 1/1960 | Swearingen et al. | 128/206.27 |
| 3,049,121 | 9/1962 | Brumfield et al. | 128/146 |
| 3,170,461 | 2/1965 | Watts, Jr. | 128/146 |
| 3,220,409 | 11/1965 | Liloia et al. | 128/146 |
| 3,288,138 | 11/1966 | Sachs | 128/139 |
| 3,316,904 | 5/1967 | Wall | 128/146.6 |
| 3,620,214 | 11/1971 | Thackston | 128/146.6 |
| 3,664,335 | 5/1972 | Boucher et al. | 128/146.6 |
| 3,688,768 | 9/1972 | Reimschussel et al. | 128/146.6 |
| 3,779,244 | 12/1973 | Weeks, Jr. et al. | 128/146.6 |
| 3,888,246 | 6/1975 | Lauer | 128/146.2 |
| 3,890,966 | 6/1975 | Aspelin et al. | 128/146.2 |
| 3,929,135 | 12/1975 | Thompson | 128/287 |
| 3,932,153 | 1/1976 | Byrns | 55/511 |
| 3,953,566 | 4/1976 | Gore | 264/288 |
| 3,971,369 | 7/1976 | Aspelin et al. | 128/146.2 |
| 3,971,373 | 7/1976 | Braun | 128/146.2 |
| 3,985,132 | 10/1976 | Boyce et al. | 128/146.2 |
| 4,187,390 | 2/1980 | Gore | 174/102 |
| 4,215,682 | 8/1980 | Kubik et al. | 128/205.29 |
| 4,319,567 | 3/1982 | Magidson | 128/206.19 |
| 4,323,063 | 4/1982 | Fisichella | 128/139 |
| 4,384,577 | 5/1983 | Huber et al. | 128/206.19 |
| 4,417,575 | 11/1983 | Hilton et al. | 128/206.19 |
| 4,419,993 | 12/1983 | Petersen | 128/201.15 |
| 4,419,994 | 12/1983 | Hilton | 128/206.19 |
| 4,454,881 | 6/1984 | Huber et al. | 128/206.15 |
| 4,495,030 | 1/1985 | Giglia | 162/145 |
| 4,510,931 | 4/1985 | Henderson et al. | 128/202.28 |
| 4,536,440 | 8/1985 | Berg | 428/284 |
| 4,547,420 | 10/1985 | Kreuger et al. | 428/229 |
| 4,551,378 | 11/1985 | Carey, Jr. | 428/198 |
| 4,600,002 | 7/1986 | Maryyanek et al. | 128/206.19 |
| 4,606,341 | 8/1986 | Hubbard et al. | 128/206.19 |
| 4,616,647 | 10/1986 | McCreadie | 128/206.19 |
| 4,619,948 | 10/1986 | Kennedy et al. | 128/205.27 |
| 4,635,628 | 1/1987 | Hubbard et al. | 128/201.17 |
| 4,641,645 | 2/1987 | Tayebi | 128/206.19 |
| 4,688,566 | 8/1987 | Boyce | 128/206.19 |
| 4,797,956 | 1/1989 | Boyce | 2/431 |
| 4,802,473 | 2/1989 | Hubbard et al. | 128/206.19 |
| 4,807,619 | 2/1989 | Dyrud et al. | 128/206.19 |
| 4,827,924 | 5/1989 | Japuntich | 428/206.12 |
| 4,850,347 | 7/1989 | Skov | 128/206.16 |
| 4,856,509 | 8/1989 | Lemelson | 128/206.19 |
| 4,873,972 | 10/1989 | Magidson | 128/206.12 |
| 4,883,052 | 11/1989 | Weiss et al. | 128/205.27 |
| 4,920,960 | 5/1990 | Hubbard et al. | 128/206.12 |
| 4,941,470 | 7/1990 | Hubbard et al. | 128/206.13 |
| 4,944,294 | 7/1990 | Borek, Jr. | 128/206.19 |
| 4,945,574 | 8/1990 | Dagher | 2/9 |
| 4,966,140 | 10/1990 | Herzberg | 128/206.19 |
| 4,969,457 | 11/1990 | Hubbard | 128/206.12 |
| 5,003,633 | 4/1991 | Itoh | 2/9 |
| 5,012,805 | 5/1991 | Muckerheide | 128/205.28 |
| 5,020,533 | 6/1991 | Hubbard et al. | 128/206.23 |
| 5,025,506 | 6/1991 | Huang | 2/206 |
| 5,033,115 | 7/1991 | Bowling | 2/51 |
| 5,035,240 | 7/1991 | Braun et al. | 128/205.27 |
| 5,094,236 | 3/1992 | Tayebi | 128/206.12 |
| 5,107,547 | 4/1992 | Scheu | 2/206 |
| 5,150,703 | 9/1992 | Hubbard et al. | 128/206.12 |
| 5,322,061 | 6/1994 | Brunson | 128/206.13 |

FOREIGN PATENT DOCUMENTS

| | | | |
|---|---|---|---|
| 867791 | 9/1941 | France. | |
| 2471792 | 6/1981 | France | 62/18 |
| 655814 | 1/1938 | Germany. | |
| 688227 | 1/1940 | Germany. | |
| 2717968 | 12/1977 | Germany | 128/335 |
| 7706660 | 6/1977 | Netherlands | 62/23 |
| 4789 | 2/1912 | United Kingdom. | |
| 5104 | 2/1913 | United Kingdom. | |
| 967455 | 12/1960 | United Kingdom. | |
| 892262 | 3/1963 | United Kingdom. | |
| 1049604 | 11/1966 | United Kingdom. | |
| 1433504 | 4/1973 | United Kingdom. | |
| 1473924 | 5/1977 | United Kingdom. | |
| 2028664 | 3/1980 | United Kingdom | A62B 23/00 |
| 1588442 | 4/1981 | United Kingdom. | |
| 2059782 | 4/1981 | United Kingdom. | |
| 2103491 | 2/1983 | United Kingdom | A62B 7/10 |
| 8101019 | 4/1981 | WIPO. | |
| 8103266 | 11/1981 | WIPO | A41D 13/00 |
| 8601734 | 3/1986 | WIPO | A62B 18/08 |
| 8900874 | 2/1989 | WIPO | A62B 18/02 |
| 8910106 | 11/1989 | WIPO | A61F 9/04 |
| 9108829 | 6/1991 | WIPO | A62B 23/02 |

OTHER PUBLICATIONS

Tecnol Fluidshield brochure, "The First Mask Specifically Designed to Resist Fluid Penetration".

W.T. Davis, "Filtration Efficiency of Surgical Face Masks: The Need for More Meaningful Standards" *American Journal of Infection Control*, vol. 19, No. 1, Feb. 1991, pp. 16–18.

Annotated Figure 2.

U.S. Patent application No. 08/278930, filed Jul. 20, 1994, and entitled, *Face Mask With Enhanced Seal and Method*.

U.S. Patent application No. 08/491137, filed Jul. 17, 1995, and entitled, *Disposable Aerosol Mask With Face Shield*.

Correspondence from AIPO dated Jul. 12, 1995 to F.B. Rice & Co. citing Australian Patent AU–B–50331/79.

Correspondence from EPO dated May 10, 1995 to Uexkull & Stolberg with European Search Report, Appl. No. EP 94 25 0231.

Annotation Fig. 2, 1 page, undated.

Tecnol, reprinted from AORN Journal, *The Mask Collection*, 1987, 4 pages.

Glendale Protective Technologies, Inc., *Glendale Dustbuster*, Jul. 1992, 1 page.

AO Safety Products, *R1050/Dust Demon Foldable, Reusable/Disposable Resprirator*, undated, 2–sided/2pages.

Tecnol, *FluidShied Surgical Masks featuring SplashGuard Visors*, Nov. 1992, 2–sided/1 page.

Tecnol, *FluidShield*, 6 pages, undated.

Wayne T. Davis, Ph.D., American Journal of Infection Control, *Filtration efficiency of surgical face masks: The need for more meaningful standards*, 1991, 3 pages.

Racal Health & Saftey, Inc., *DELTA Disposable Respirators*, 1993, 4 pages.

United States Patent application No. 08/278930 filed Jul. 20, 1994 entitled *Face Mask with Seal and Method*, allowed.

United States Patent application No. 08/374,321 filed Jan. 18, 1995 entitled *Face Mask with Enhanced Facial Seal*, Pending.

United States Patent application No. 08/491,137 filed Jul. 17, 1995 entitled *Disposable Aerosol Mask with Face Shield*, Pending.

United States Patent application No. 08/571,300 filed Dec. 12, 1995 entitled *Face Mask with Enhanced Seal and Method*, Pending.

European Search Report for Application No. 95305033.3 dated Jan. 2, 1997.

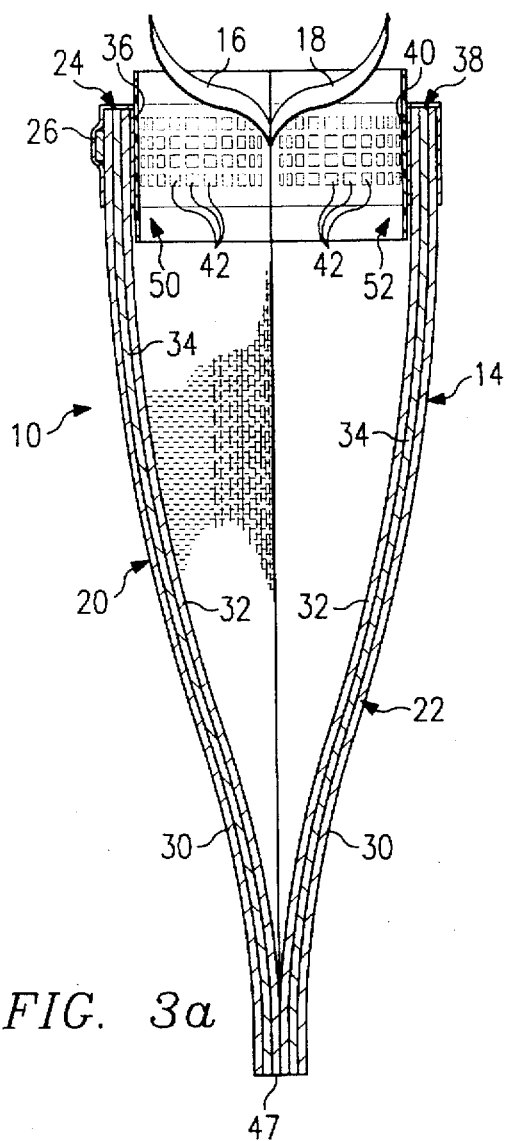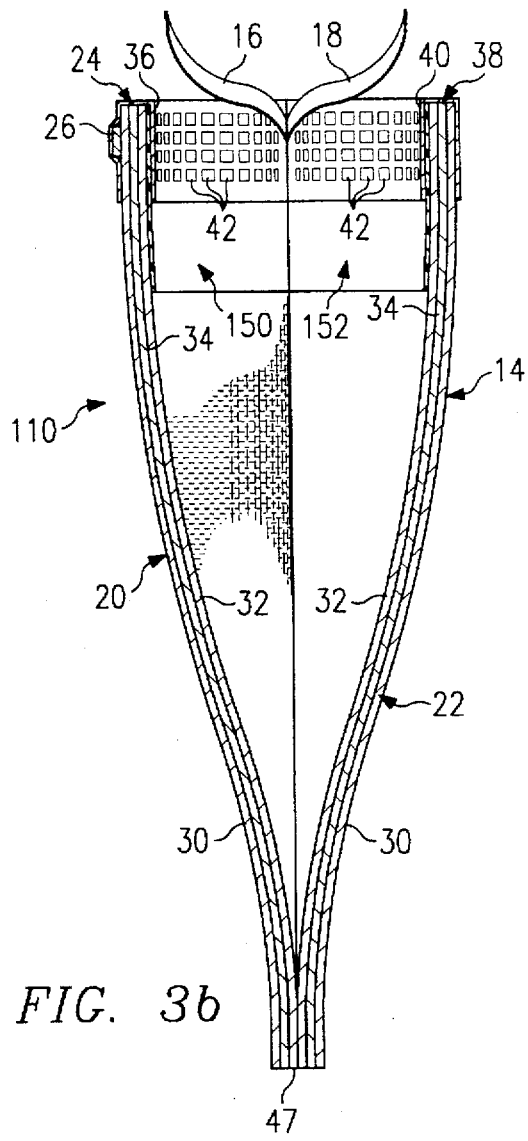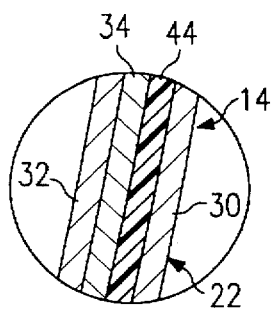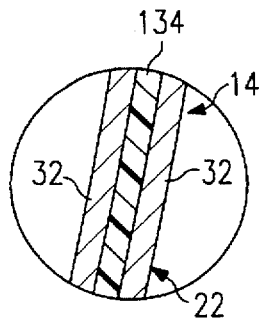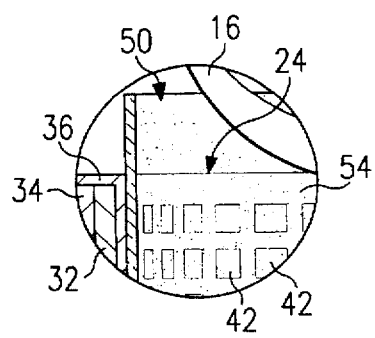

DISPOSABLE FACE MASK WITH ENHANCED FLUID BARRIER

RELATED APPLICATIONS

"This application is a Continuation-in-Part application of pending U.S. patent application Ser. No. 08/168,090 filed Dec. 15, 1993, entitled *Disposable Face Mask with Face Shield*, of same assignee, now abandoned in favor of U.S. patent application Ser. No. 08/491,137 filed Jul. 17, 1995, and of U.S. patent application Ser. No. 08/278,930 filed Jul. 20, 1994, entitled *Face Mask with Enhanced Seal and Method*, of same assignee, now U.S. Pat. No. 5,553,608. This application is related to U.S. patent application Ser. No. 07/991,154 filed Dec. 16, 1992, entitled *Disposable Face Mask*, of same assignee, now U.S. Pat. No. 5,322,061."

TECHNICAL FIELD OF THE INVENTION

This invention relates generally to face masks capable of preventing the passage of airborne aerosols, particulate matter and/or liquids. More particularly, and not by way of limitation, this invention relates to disposable face masks having an enhanced fluid barrier between the periphery of the mask and a wearer's face. Also, this invention allows using various materials to enhance the filtration capabilities of the resulting mask for the specific operating environment while maintaining good breathability.

BACKGROUND OF THE INVENTION

Disposable face masks have been manufactured for many years. In the medical field, many of these early masks were used in preventing contamination of a patient by the breath of health care personnel. In recent years with increased concern for infection of health care personnel with airborne pathogens, such as the hepatitis B virus, it has become necessary to not only prevent contamination of patients due to exhalation from health care personnel, but also to prevent infection of health care personnel due to inhalation of airborne infection particles. It has become even more important in view of the advent of human immunodeficiency virus (HIV) and the recent increase in infectious tuberculosis associated with many HIV patients.

The rapid increase of infectious diseases, particularly AIDS, has made the use of such protective equipment increasingly important. The Center for Disease Control in Atlanta, Ga., has found that the AIDS virus (HIV) can be passed by contact with body fluids. Contact of AIDS contaminated body fluids with another person's source of body fluids, e.g., eyes, nose, mouth, etc., can pass the disease. Therefore, it is necessary to prevent a patient's body fluids from contacting the face of health care personnel.

Aerosols having airborne liquid and solid particles are generated not only by the exhalation of infected patients, but also by certain procedural manipulations and processes that impart energy to any liquid or microbial suspension. Surgical procedures involving use of drills and saws are particularly prolific producers of aerosols which may contain tuberculosis, HIV or other pathogens from an infected patient. Concern with tuberculosis has been increasing since new strains of the disease show strong resistances to multiple types of drug treatment.

One type of mask is illustrated in U.S. Pat. No. 2,012,505 entitled Mask, issued on Aug. 27, 1935 to S. J. Goldsmith. Another type of disposable face mask is illustrated in U.S. Pat. No. 4,319,567 entitled Disposable Face Mask, issued on Mar. 16, 1982 to M. Magidson. This mask is molded and has been especially configured in an effort to avoid leakage of fluid flow past the edges of the mask. Obviously, leakage cannot be tolerated when attempting to control liquids and/or aerosols. U.S. Pat. No. 4,606,341 entitled Noncollapsible Surgical Face Mask, issued Aug. 19, 1986 to Vance M. Hubbard and Welton K. Brunson shows a conventional rectangular face mask having a trapezoidal pleat. For some operating conditions, rectangularly shaped masks, including the mask shown in Patent '341, may have less than an optimal fit to prevent the passage of liquids and aerosols between the periphery of the masks and a wearer's face.

Recent developments in surgical face mask have resulted in resistance to liquid penetration from the exterior of such masks. U.S. Pat. No. 4,920,960 entitled Body Fluids Barrier Mask, issued on May 1, 1990 to Hubbard, et al., is exemplary of improvements in such masks. U.S. Pat. No. 5,020,533 entitled Face Mask with Liquid and Glare Resistant Visor, issued on Jun. 4, 1991 to Hubbard, et al., is an example of incorporating a visor to protect the face of a wearer from liquids during medical procedures.

SUMMARY OF THE INVENTION

In accordance with the present invention, a disposable face mask is provided to substantially reduce or eliminate the shortcomings previously associated with disposable face masks. A disposable face mask incorporating the present invention provides an effective fluid barrier or seal with the face of a wearer, higher filtration capability with respect to aerosols, a sufficiently low pressure drop through the mask for comfortable breathing, and protection from liquid splashes or liquid sprays. For some applications the disposable face mask may include one or more layers of selected materials such as expanded polytetrafluoroethylene to enhance the filtration capability of the resulting mask.

In one aspect, this invention provides a disposable face mask comprising a filter body for covering the nose and mouth of a wearer. The body has top and bottom edges with the top edge arranged to extend across the bridge of the nose of the wearer and the bottom edge arranged to extend under the wearer's chin. A layer of gasket-type sealing material is preferably secured adjacent to the top edge and the bottom edge. A first securing member may be attached to the body adjacent each end of the top edge and disposed generally about the back of the head of the wearer in an approximate linear continuation of the top edge urging the top edge into tight engagement with the wearer's face to prevent fluid flow between the top edge and the wearer's face. A second securing member may be attached to the body adjacent to each end of the bottom edge and disposed generally over the top of the wearer's head in an approximate linear continuation of the bottom edge urging the bottom edge into tight engagement with the wearer's face to prevent fluid flow between the bottom edge and the wearer's face. The resulting mask provides an enhanced fluid barrier around the periphery of the mask to prevent the bypass of both liquids and aerosols between the edges of the mask and the wearer's face.

In another aspect, the present invention provides a surgical style disposable face mask which inhibits the passage of fluids between the periphery of the mask and the wearer's face while providing enhanced comfort to the wearer. The present invention may be used with standard pleated style face masks or off-the-face style masks by attaching a layer of gasket-type sealing material adjacent to top and bottom edges of the respective mask. For some applications, a single pair of ties may be used to secure a mask incorporating the present invention with the head and face of the wearer. For other applications, a mask incorporating the present invention may be secured to the head and face of the wearer with a pair of ear loops, four surgical tie strips or a continuous loop of resilient material. Fluid impervious flaps may be included to extend the coverage area of the face mask and improve the fluid seal in cooperation with the gasket-type sealing material between the periphery of the mask and the face of the wearer.

A further aspect of the present invention includes combining gasket-type sealing material disposed on the periphery of the respective face mask with securing means formed from resilient material to provide comfort to the wearer while maintaining a tight peripheral seal for long periods of time. The securing means may be formed from various types of material as desired. For some applications, the gasket-type sealing material may be placed on the interior surface of a generally rectangular surgical style face mask along the top and bottom edges and along each side of the face mask.

The present invention provides significant technical advantages by forming a barrier which prevents the passage of liquids and aerosols between the periphery of the mask and the wearer's face. The resulting face mask blocks liquid spray and aerosols from passing through the exterior of the mask or around the edges of the face mask and contacting portions of the wearer's face. The mask provides substantially increased flow area for the passage of air through the mask during normal breathing by the wearer while at the same time allowing the use of filtration media having higher resistance to the passage of liquids and aerosols through the mask. The present invention allows optimizing the filtration capability for resistance to the passage of aerosols while minimizing the restriction to normal breathing caused by wearing the mask and allows for a substantially enhanced fit between the periphery of the mask and the contours of a wearer's face.

Further technical advantages of the present invention include the use of a filter media formed from expanded polytetrafluoroethylene (PTFE) membrane with one or more layers of bicomponent polyethylene or polypropylene disposed on opposite sides of the filter media. Gasket-type seals may be formed in accordance with the teachings of the present invention to provide an effective fluid barrier between the periphery of both pleated and non-pleated type face masks and the wearer's face. The gasket-type seals may be formed by thin layers of plastic film materials such as polyethylene and polypropylene. For other applications, various types of hydrogel may be disposed on the periphery of the associated face mask in combination with or as a replacement for the gasket-type sealing material.

A further aspect of the present invention includes placing gasket-type sealing material on the interior surface of a face mask to form a fluid barrier with the wearer's face. By forming a gasket-type seal in accordance with the teachings of the present invention, normal movement of the face mask associated with breathing and talking by the wearer will not compromise the fluid barrier formed between the gasket-type sealing material and the wearer's face.

BRIEF DESCRIPTION OF THE DRAWINGS

For a more complete understanding of the present invention and advantages thereof, reference is now made to the following description taken in conjunction with the accompanying drawings, in which:

FIG. 3a is a drawing in section and in elevation with portions broken away of the mask shown in FIG. 1 taken generally along lines 3a—3a of FIG. 2;

FIG. 3b is a drawing in section and in elevation with portions broken away showing a disposable face mask incorporating an alternative embodiment of the present invention;

FIG. 3c is an enlarged sectional view with portions broken away showing an alternative embodiment of the mask of FIG. 1 with four layers of material including at least one liquid impervious layer;

FIG. 3d is an enlarged sectional view with portions broken away showing another alternative embodiment of the mask of FIG. 1 with three layers of material including at least one layer of expanded PTFE filter media;

FIG. 3e is an enlarged drawing with portions broken away showing a further alternative embodiment with hydrogel placed on gasket-type sealing material attached to the interior periphery of the mask of FIG. 1;

DETAILED DESCRIPTION OF THE INVENTION

The preferred embodiments of the present invention and its advantages are best understood by referring to FIGS. 1–7 of the drawings, like numerals being used for like and corresponding parts of the various drawings.

Disposable face masks 10, 110, 210 and 310 incorporating various features of the present invention may be used to retard the flow of bacteria, liquids, particulate matter and aerosols from the exterior of the respective mask to the nose and mouth of a wearer. For purposes of this application aerosols are defined as insoluble liquids or particulate matter frequently associated with microbial solutions. The term "fluid" is used within this application to include any gas, liquid, or mixture of gas and liquid. Various types of particulate matter and aerosols may be entrained with such fluids.

The present invention forms a gasket-type seal to provide an enhanced fluid barrier between the periphery of a disposable face mask and the face of a wearer. For purposes of this application, the term "gasket-type seal" means a fluid barrier or pressure tight seal formed by placing a deformable material between two relatively stationary objects. Such gasket-type seals are sometimes referred to as "static seals." A wide variety of gasket-type sealing materials including thin plastic films and/or hydrogels, may be satisfactorily used to form a gasket-type seal between the periphery of a face mask and the face of a wearer in accordance with the teachings of the present invention. Other types of deformable material such as open cell and closed cell foams may also be used to form the desired gasket-type seal.

The present invention allows optimizing the filtration capability of a disposable face mask to resist the passage of liquids, particulate matter and/or aerosols while at the same time minimizing resistance to normal breathing by a wearer and providing a comfortable fit for extended periods of wear.

The present invention allows using one or more multiple layers of filter media which may be specifically designed to block the passage of aerosols in addition to liquids.

Figure 1:
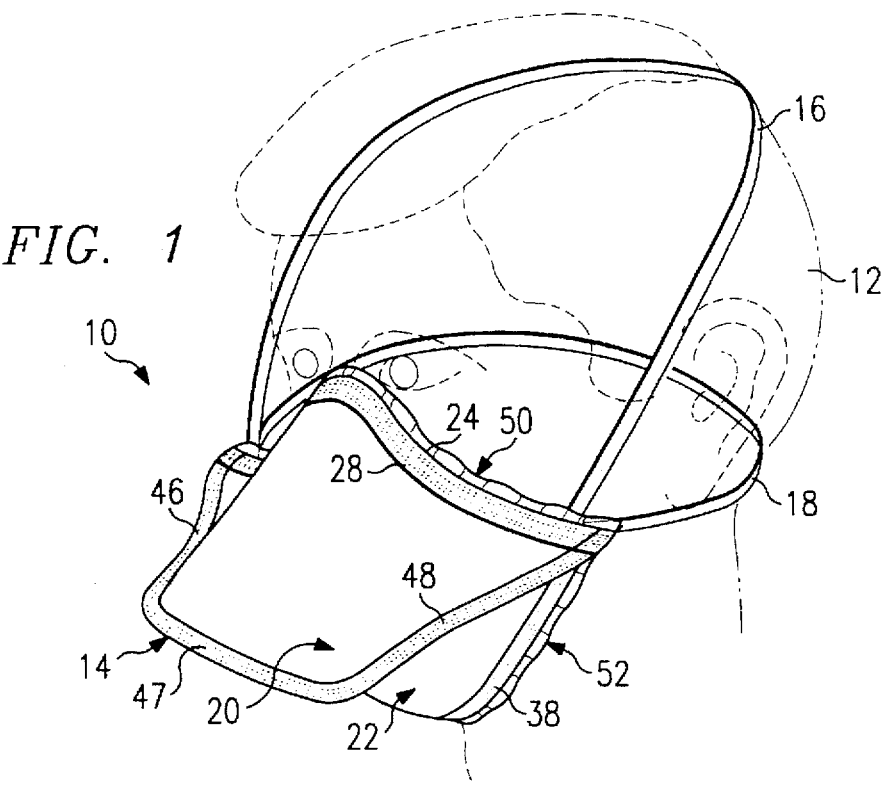
FIG. 1 is a perspective view of a disposable face mask incorporating an embodiment of the present invention illustrated on the head of a wearer.

Mask 10 incorporating some of the teachings of the present invention in shown in FIG. 1 as being positioned on the face of wearer 12 who is illustrated in ghost lines. Mask 10 includes filter body 14 which is secured to wearer 12 by resilient securing members or headbands 16 and 18. Filter body 14 comprises an upper portion 20 and a lower portion 22 which have a generally trapezoidal configuration. Upper and lower portions 20 and 22 preferably have matching exterior dimensions and shape. Upper and lower portions 20 and 22 may be bonded together by heat and/or ultrasonic sealing along three sides of filter body 14. Bonding in this manner adds important structural integrity to mask 10.

Figure 2:
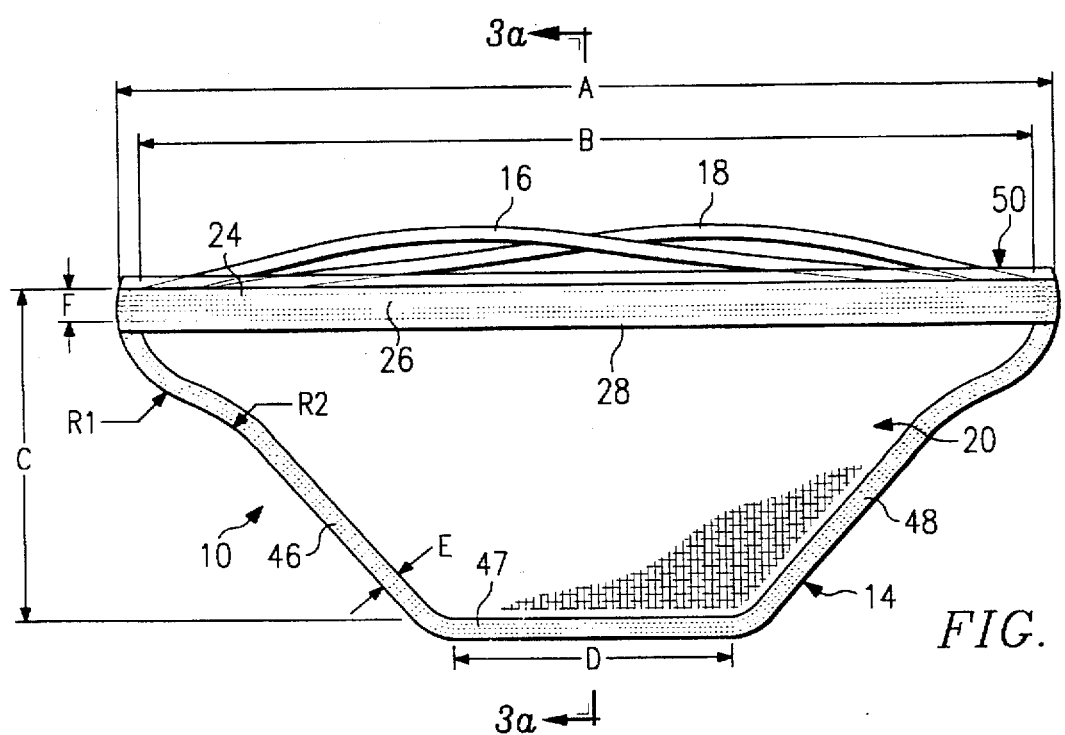
FIG. 2 is the plan view of the mask shown in FIG. 1.

The fourth side of filter body 14 is open and includes a top edge 24 with an elongated malleable member 26 (see FIGS. 2 and 3a). Malleable member 26 is provided so that top edge 24 of mask 10 can be configured to closely fit the contours of the nose and cheeks of wearer 12. Malleable member 26 is preferably constructed from an aluminum strip with a rectangular cross-section, but may also be a moldable or malleable steel or plastic member.

Top edge 24 of upper portion 20 and bottom edge 38 of lower portion 22 cooperate with each other to define the periphery of mask 10 which contacts the face of wearer 12. The present invention allows optimizing the barrier formed between the periphery of mask 10 and the face of wearer 12 and the filtration capability of mask 10 to resist the passage of liquids, particulate matter and aerosols through filtration media 34 while minimizing resistance to normal breathing of wearer 12 resulting from the use of mask 10. The present invention also allows including multiple layers of filter media within filter body 14 including layer 44 of liquid impervious material.

As shown in FIGS. 1 and 3a, mask 10 has the general shape of a cup or cone when placed on the face of wearer 12. The present invention allows mask 10 to provide "off-the-face" benefits of a molded-cone style mask while still being easy to package, store and ship. "Off-the-face" style masks provide a larger breathing chamber as compared to soft, pleated masks which contact a substantial portion of the wearer's face. Therefore, "off-the-face" style masks generally permit cooler and easier breathing.

The present invention allows optimizing the volume of air contained within filter body 14. If the volume is too large, excessive amounts of exhaled air may be retained within filter body 14 at normal breathing rates. By properly selecting the size of filter body 14, excessive heating of the air within filter body 14 is minimized and dizziness from prolonged periods of rebreathing exhaled air is also minimized.

The approximate optimum dimensions for mask 10 as shown in FIG. 2 include 10¼ inches for the major length, dimension A, of the trapezoidal shape of filter body 14. The length of the opening in filter body 14 defined in part by top edge 24 and bottom edge 38, dimension B, is 9¼ inches due to approximately ½ inches of seal at each junction between upper portion 20 and lower portion 22. The minor length of the parallel portion of trapezoid shaped filter body 14, dimension D, is approximately 3$\frac{5}{16}$ inches. The opening of filter body 14 defined in part by dimensions A and B is generally parallel with minor length, dimension D. Dimensions A and B may be varied by ±¾ inches. The width of the trapezoid shape of filter body 14, dimension C, is 3½ inches. Dimensions C and D may be varied by ±¼ inches. The bonded border defining the three closed sides of mask 10, dimension E, is preferably ¼ inches in width. The inner portions of top edge 24 and bottom edge 38 which contact the wearer's face, dimension F, are approximately ½ inches in width.

Strips of gasket-type sealing material 50 and 52 are preferably disposed on the inner portion of top edge 24 and bottom edge 38 respectively. Strips 50 and 52 preferably have approximately the same length as dimension A of filter body 14 and a width of approximately 1¼ inches. For one application, strips 50 and 52 have a thickness of approximately 0.0005 inches.

The above dimensions may be modified to accommodate wearers having smaller or larger facial features. However, the ratio between the width of the trapezoid shape which defines mask 10, dimension C, as compared to the minor length of the trapezoid shape, dimension D, should preferably remain at approximately 1 to 1. The preferred ratio between the major length of filter body 14, dimension A, and the minor length, dimension D, is approximately 3 to 1. For other applications, the ratio of dimension A to dimension D may be varied to provide the desired fit as long as dimension A is larger than dimension D and the width is approximately equal to dimension C. Strips 50 and 52 of gasket-type sealing material allow face mask 10 to form a fluid tight barrier with wearers having a wider variety of facial features.

An important feature of the present invention is forming radius R1 of approximately 1⅛ inches and radius R2 of approximately 3 inches in the non-parallel or angled sides of filter body 14. Radii R1 and R2 cooperate with each other and with the three bonded sides of filter body 14 to prevent collapse of filter body 14 during normal breathing by wearer 12. These radii, R1 and R2, help mask 10 retain the desired, off-the-face shape during normal breathing. If the sealed border on the three closed sides of filter body 14 is less than ¼ inches, mask 10 may tend to collapse during normal breathing. Therefore, an important feature of the present invention includes combining radii R1 and R2 with a sealed border of approximately ¼ inches in width or greater to provide the desired cone or cup shaped mask covering the nose and mouth of wearer 12 and to maintain a fluid tight barrier with wearer 12's face without collapsing during normal breathing.

Radius R2 curves outward from opposite sides of mask 10 and is tangent to radius R1 that curves inward towards the attachment points for headbands 16 and 18. This arrangement serves several important functions. Radii R1 and R2 cooperate with each other and strips 50 and 52 to improve the facial seal performance between the periphery of mask 10 and the face of wearer 12. Radii R1 and R2 allow mask 10 to open with relatively flat surfaces near each end of top edge 24 and bottom edge 38 adjacent to the attachment point for headbands 16 and 18. These flat surfaces adjacent to the attachment points for the headbands 16 and 18 gradually taper away from the opening in filter body 14. The general trapezoidal shape of filter body 14 in cooperation with radii R1 and R2 and the other preferred dimensions and ratios cooperate to minimize collapse of filter body 14 during normal use of mask 10.

Radii R1 and R2 cooperate with strips 50 and 52 disposed respectfully on the inner portion of top edge 24 and bottom edge 38 to allow mask 10 to fit securely with and to form a tight facial seal with a greater number of different face sizes. Mask 10 is particularly useful with smaller faces which contact the tapered surfaces adjacent to the attachment points for headbands 16 and 18 on the interior of mask 10 as shown in FIGS. 3a and 3b. Other types of surgical mask may also benefit from placing strips 50 and 52 of gasket-type sealing material between the periphery of the respective mask and the face of the wearer.

Radii R1 and R2 assist in maintaining the integrity of mask 10 by providing strength along the three-bonded sides of filter body 14 when mask 10 is fully opened against the face of a wearer. These previously described design features allow for the use of lighter weight or lighter basis material which adds breathability and comfort to mask 10. Without radii R1 and R2 these same lightweight materials would be prone to collapse during inhalation. The ¼ inches bonded seal around the three closed sides of filter body 14 contributes to maintaining structural integrity of mask 10 when secured to the face of wearer 12.

Various adhesives, ultrasonic seals and/or heat seals may be used to attach strips 50 and 52 of gasket-type sealing material respectively to top edge 24 and bottom edge 38. Ultrasonic seals (sometimes referred to as ultrasonic welds) 42 have been found to be particularly advantageous for attaching strips 50 and 52. For some applications strips 50 and 52 may be formed from polyethylene or polypropylene with a thickness between 0.005 and 0.0005 inches. However, other types of thin film and deformable materials with various thicknesses may be satisfactorily used with the present invention.

Blow-by associated with normal breathing of wearer 12 is substantially eliminated by properly selecting the dimension and location of malleable strip 26 and gasket-type sealing material 50 with respect to top edge of 24. Malleable strip 26 is preferably positioned in the center of top edge 24 and has a length in the range of fifty percent to seventy percent of the total length, dimension A, of top edge 24. For one embodiment of the present invention, the performance of mask 10 was enhanced by using malleable strip 26 manufactured from quarter-tempered aluminum. For this embodiment, the length of malleable strip 26 was approximately 54 percent of the length of top edge 24 with a thickness of 0.021 inches and a width of 0.197 inches.

The present invention allows designing mask 10 with the optimum periphery to fit the face of wearer 12 and the optimum dimension for strips 50 and 52 to form an enhanced fluid barrier with the nose and face of wearer 12. The present invention allows modification to the length of top edge 24 and bottom edge 38 while maintaining approximately the same surface area for normal breathing through filter media 34.

For some applications securing members 16 and 18 are preferably constructed from resilient polyurethane, but may be constructed from elastic rubber or a covered stretch yarn. The covered stretch yarn may consist of an elastomeric material wrapped with nylon or a polyester. For other applications securing members 16 and 18 may comprise double knitted headbands such as circle knitted polyester/LYCRA or nylon/LYCRA. The use of resilient securing members 16 and 18 substantially improves the fluid barrier between the periphery of mask 10 and the face of wearer 12.

As illustrated in FIG. 3a, upper and lower portions 20 and 22 each include an outer mask layer 30 that is preferably constructed from a spun-bonded polypropylene. Outer mask layers 30 may also be constructed from a bi-component and/or powder bonded material such as polyethylene or polypropylene, a cellulastic tissue, or a spun-bonded polyester. Outer mask layers 30 typically have a basis weight range of 0.5 ounces per yard to 1.0 ounces per yard. 0.9 ounces per yard is one of the preferred basis weights for outer layers 30.

Inner mask layers 32 are preferably composed of a bicomponent polyethylene and polypropylene. Layers 32 may also be constructed from polyester and/or polyethylene material or cellulastic tissue. Layers 32 typically have a basis weight range of 0.4 ounce per yard to 0.75 ounces per yard. 0.413 ounces per yard is one of the preferred basis weights for layers 32. One or more intermediate layers of filter media may be disposed between outer mask layer 30 and inner mask layer 32. Selection of the number and type of intermediate layers of filter media will depend upon the intended use and function for mask 10.

In FIG. 3a, filter body 14 is shown with only one intermediate mask layer 34 which comprises the filter media for the associated mask 10. This layer is preferably constructed from a melt-blown polypropylene, but may be constructed from an extruded polycarbonate, a melt-blown polyester, or a melt-blown urethane.

As shown in both FIGS. 3a and 3b, top edge 24 of masks 10 and 110 may be faced with edge binder 36 that extends across the open end of mask 10 and covers malleable strip 26. In a similar manner, bottom edge 38 of face masks 10 and 110 may be encompassed in edge binder 40. Edge binders 36 and 40 are preferably constructed from a spunlaced polyester material. Binders 36 and 40 may also be constructed from a number of thermally bonded bicomponent materials or from polypropylene or polyethylene nonporous plastic films. Strips 50 and 52 are disposed on the interior of filter body 14 adjacent respectively to edge binders 36 and 40.

A plurality of sonic bonds 42 are used to attach respectively to strip 50 with edge binder 36 and layers 30, 32 and 34 at top edge 24, and strip 52 with edge binder 40 and layers 30, 32 and 34 at bottom edge 38. For face mask 10, the middle portion of strip 50 and 52 are attached respectively to the interior of filter body 14 with approximately ¼ inches of gasket-type sealing material extending outwardly from top edge 24 and bottom edge 38. Also, approximately ¼ inches of gasket-type sealing material 50 and 52 extends respectively from sonic bonded area 42 into the interior of filter body 14.

Face mask 110 shown in FIG. 3b is similar to face mask 10 except strip 150 and 152 are disposed within the respective edge binders 36 and 38 such that strips 150 and 152 only extend inwardly within filter body 14. Strips 150 and 152 do not extend from top edge 24 and bottom edge 38 as shown for mask 10. FIGS. 3a and 3b thus show only two of the many options available for installing strips of gasket-type sealing material adjacent to the top edge and bottom edge of a face mask in accordance with the teachings of the present invention.

FIG. 3c shows an alternative embodiment of the present invention in which filter body 14 includes two intermediate layers 34 and 44 of filter media. Layer 44 may be formed from a barrier material that is gas permeable and permits gas (air) to pass through filter body 14 in both directions and is impermeable to liquid passing through mask 10 in at least one direction. Layer 44 is preferably arranged to prevent the passage of liquids from the exterior of filter body 14 through layer 44 to the interior of filter body 14.

A more complete description of the construction and operation of such material can be found in U.S. Pat. No. 3,929,135 entitled Absorptive Structure Having Tapered Capillaries, issued on Dec. 30, 1975 to Hugh A. Thompson. Such materials are often constructed from a low density polyethylene and include small apertures which prevent liquids from passing therethrough due to the liquid's relatively high surface tension. U.S. Pat. Nos. '960; '533 and 5,150,703 entitled Liquid Shield Visor for a Surgical Mask with a Bottom Notch to Reduce Glare, issued on Sep. 29, 1992 to Hubbard, et al provide additional information on materials which may be used for layers 30, 32, 34 and 44 and face masks constructed with such materials. These patents are incorporated by reference for all purposes within this application. Other types of microporous film may be satisfactorily used with the present invention.

The use of barrier materials such as layer 44 is particularly important when mask 10 is worn in an environment where the wearer may be exposed to "body fluids". These fluids such as blood, urine and saliva may contain highly contagious germs and viruses. Contact of AIDS-contaminated body fluids with another person's source of body fluids, such as the eyes, nose and mouth, may transmit the disease. Therefore, it is often preferable to include layer 44 which is resistant to the passage of liquids through filter body 14 to prevent body fluids from contacting the nose and mouth of the wearer.

FIG. 3d shows another alternative embodiment of the present invention in which filter body 14 includes intermediate layer 134 of filter media disposed between layers 32. For this particular embodiment of the present invention the inner and outer mask layers 32 are formed from the same type of material. However, various types of material may be used with intermediate mask layer 134.

For one embodiment of the present invention intermediate mask layer 134 was formed from an expanded polytetrafluoroethylene (PTFE) membrane. Such materials are manufactured by W. L. Gore & Associates. A more complete description of the construction and operation of such materials can be found in U.S. Pat. No. 3,953,566 entitled Process for Producing Porous Products, issued on Apr. 27, 1976 to Robert W. Gore, and U.S. Pat. No. 4,187,390 entitled Porous Products and Process Therefor, issued on Feb. 5, 1980 to Robert W. Gore. These patents are incorporated by reference for all purposes within this application. For some applications and operating environments the use of filter media 134 substantially enhances the performance of the resulting disposable face mask 10.

As demonstrated by the previous comments, the generally trapezoidal shape of filter body 14 including the preferred ratios for the dimensions of filter body 14, radii R1 and R2, the width of bonded sides 46, 47 and 48 and strips 50 and 52 of gasket-type sealing material allows a wide variety of materials to be used in the manufacturer of the mask layers which comprise filter body 14. The present invention has significantly increased the types of material which may be satisfactorily used in constructing filter body 14. The present invention also allows more options with respect to selecting the number of layers of material used to manufacture filter body 14.

Referring to FIG. 1, mask 10 is illustrated as being located on the face of wearer 12. Upper portion 20 with malleable member 26 located in top edge 24 and strip 50 of gasket-type sealing material conform very closely to the configuration of the nose and cheeks of wearer 12. It is also important that bottom edge 38 with strip 52 fit very closely with the chin of wearer 12 and top edge 24 with strip 50 and the nose and cheeks of the wearer 12 fit very closely since any leaks result in bypass or blow-by of air either entering mask 10 or being discharged from mask 10 when used by wearer 12. Strips 50 and 52 substantially reduce such leakage.

Accordingly, securing members 16 and 18 have their ends attached at the junctures between top edge 24 and bottom edge 38 of mask 10 as shown in FIG. 3a. The arrangement is such that securing member 16 can be placed over the top of the head of wearer 12, as illustrated in FIG. 1, in alignment with bottom edge 38 of mask 10 so that a direct force is exerted along that line urging bottom edge 38 into sealing engagement with the chin of wearer 12. Similarly, securing member 18 is positioned around the lower base of the skull and in direct alignment with top edge 24 of mask 10 and thus placing a force thereon which tends to move top edge 24 into tighter sealing engagement with the nose and cheeks of wearer 12. As shown in FIG. 3a, the ends of securing members 16 and 18 are secured at the same location between top edge 24 and bottom edge 38 with no gap between the ends of securing members 16 and 18. The position of attaching securing members 16 and 18 to filter body 14 in cooperation with radii R1 and R2 results in the optimum pull angle to form a fluid tight barrier between strips 50 and 52 disposed on the interior of mask 10 and the face of wearer 12.

In addition to having a tight peripheral seal, it is essential that mask 10 have good breathability characteristics. That is, mask 10 should require a low differential in pressure to permit air to flow easily through filter body 14 despite the fact that layers 30, 32 and 34 are formed from material which will filter 1 micron and smaller particles and have a very tight fit between strips 50 and 52 and the face of wearer 12. A low differential pressure for air flow indicates good breathability through a mask 10 and helps to maintain the desired gasket-type seal between the periphery of mask 10 and the face of wearer 12.

For one embodiment upper portion 20 and lower portion 22 of mask 10 have a combined surface area through which air can flow of about two hundred and fifty square centimeters (250 cm$^2$). Thus, body 14 of mask 10 has a surface area of approximately two hundred and fifty square centimeters which provides enhanced breathability for wearer 12. Tests were run utilizing a flow rate of thirty-two (32) liters per minute across the entire flow area. Approximately thirty masks incorporating the present invention were checked. The masks had a pressure differential ranging from 0.9 to 1.3 mm of water with a mean pressure differential across the mask of about 1.25 mm of water. Such a low differential in pressure across the mask provides excellent breathability characteristics despite the ability of the mask to filter one micron and smaller sized particles with essentially zero edge leakage around the periphery of mask 10.

Upper portion 20 and lower portion 22 are shown connected with each other by heat sealing or ultrasonic bonding along sides 46, 47 and 48 to form filter body 14 having a general trapezoidal shape with an open side defined by top edge 24 and bottom edge 38. Securing members 16 and 18 are attached to the corners of top edge 24 and bottom edge 38 at the junction with upper portion 20 and lower portion 22 during ultrasonic bonding of sides 46, 47 and 48 of filter body 14.

In FIG. 3, layer 54 of hydrogel is shown disposed on strip 50 to further enhance the fluid barrier formed with the face of wearer 12. Various types of hydrogel and other adhesives may be satisfactorily used with the present invention to provide a sticky or tacky surface on strip 50 to contact adjacent portions of the face of wearer 12. This feature of the present invention will be discussed later in more detail.

Figure 4:
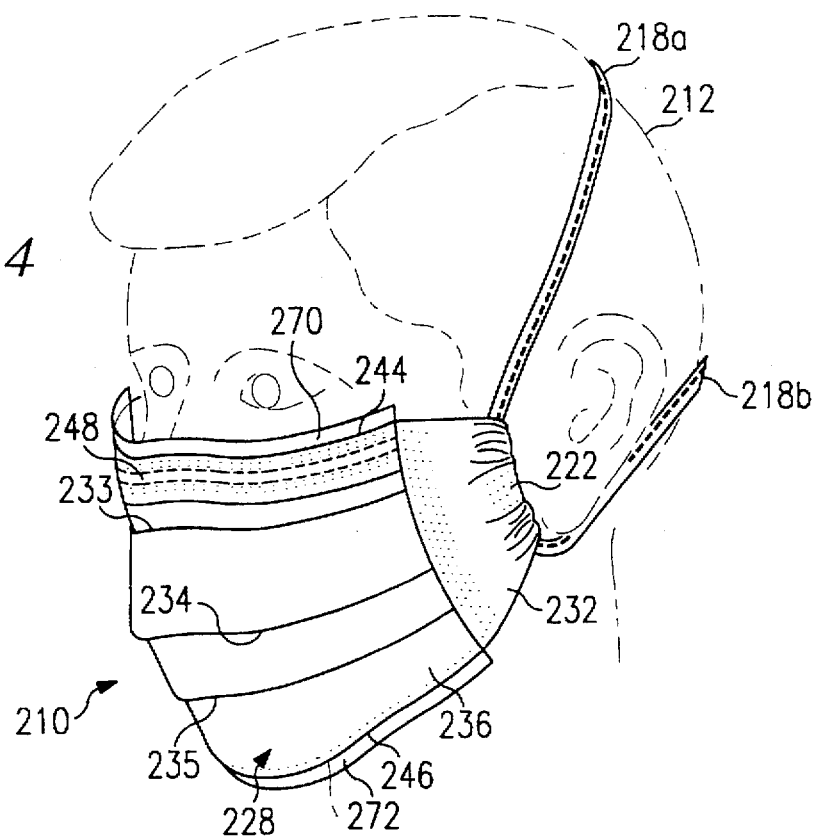
FIG. 4 is a prospective view of a disposable face mask incorporating still another embodiment of the present invention illustrated on the head of a wearer.
Figure 5:
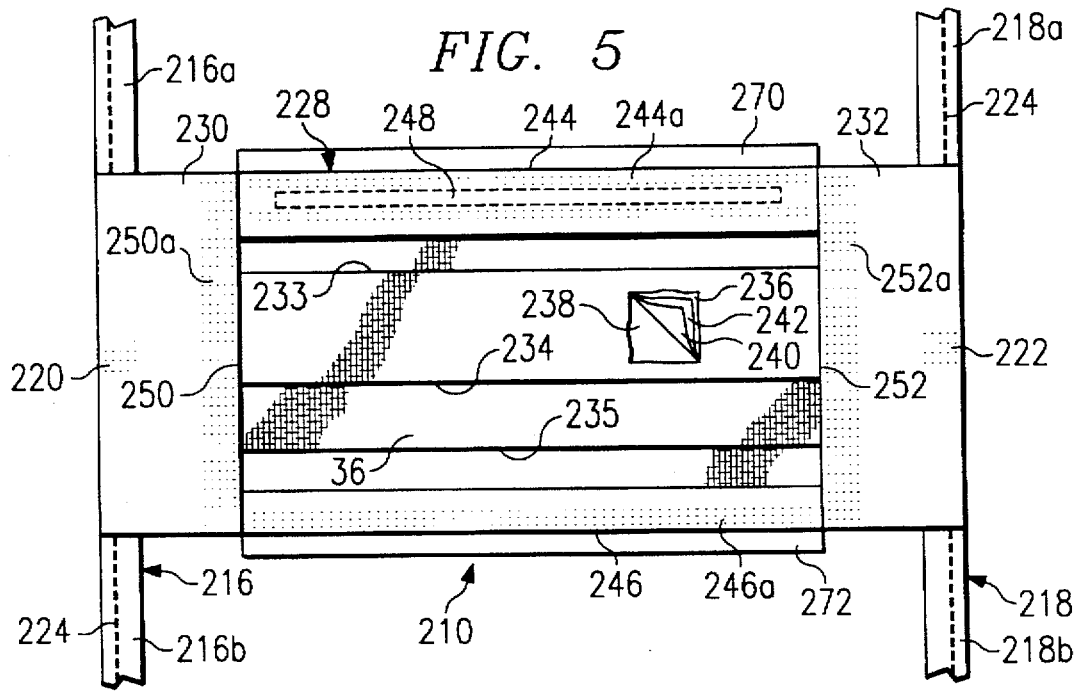
FIG. 5 is a front plan view of the mask shown in FIG. 4.
Figure 6:
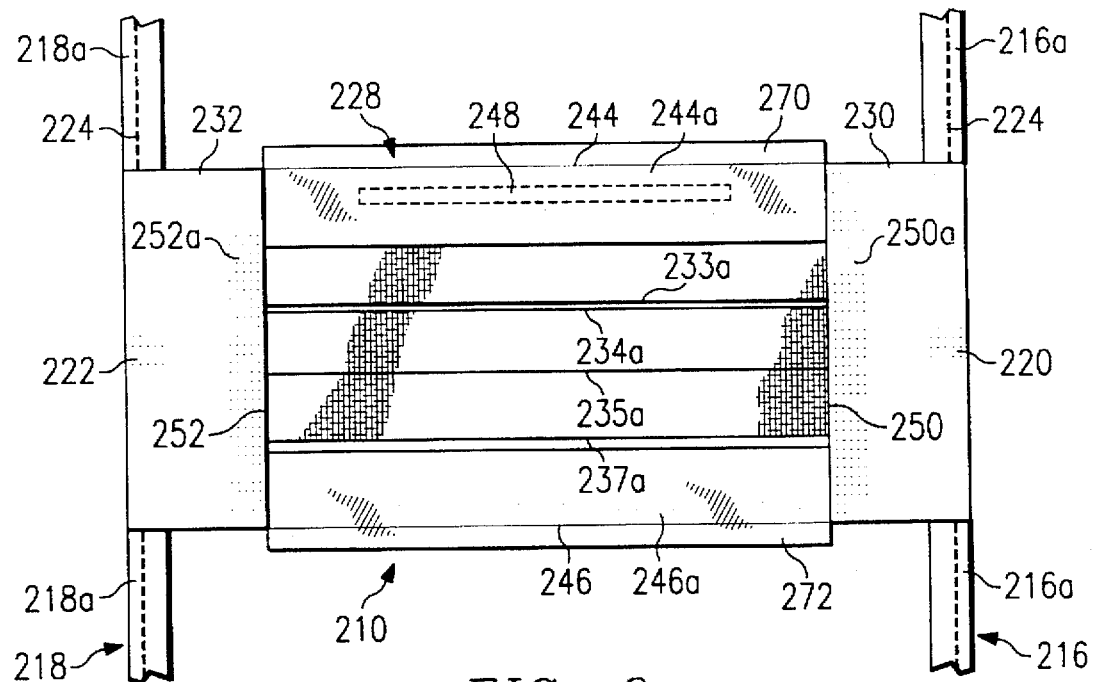
FIG. 6 is a back plan view of the mask shown in FIG. 4.

Mask 210 incorporating an alternative embodiment of the present invention is shown in FIGS. 4, 5 and 6. Mask 210 includes filter body 228 with flaps 230 and 232 extending respectively from each side of filter body 228. As will be explained later in more detail, strips 270 and 272 of gasket-type sealing material may be disposed respectively adjacent to top edge 244 and bottom edge 246. For some applications, filter body 228 may be fabricated in general as described in U.S. Pat. No. 4,635,628 entitled Surgical Face Mask with Improved Moisture Barrier and U.S. Pat. No. 4,969,457 entitled Body Fluids Barrier Mask. Both of these patents are incorporated by reference for all purposes within this application.

Flaps 230 and 232 are preferably formed from fluid impervious material folded with a generally U-shaped cross section. Flaps 230 and 232 may sometimes be referred to as C-folds. For one application of the present invention, flaps 230 and 232 may be formed from polyethylene film laminated to a non-woven material. The non-woven material may also be hydro( ) entangled. For other applications, the polyethylene film may be laminated to any type of material as desired. The polyethylene film layer may be color coded to correspond with different applications for using the resulting face mask.

For still other applications, a breathable type film may be used to form flaps 230 and 232. For further applications, flaps 230 and 232 may be formed from resilient and/or stretchable materials. Such resilient materials include thermoplastic rubbers which may be extruded or injection molded as strips or sheets of material. An example of such thermoplastic rubbers is available under the trademark KRATON® from Shell Oil Company.

One of the benefits of the present invention is the ability to form flaps 230 and 232 from materials that have lower cost as compared to the material used to form filter body 228. Another benefit of the present invention is the ability to form strips 270 and 272 along with flaps 230 and 232 from a wide variety of materials which provide an enhanced fluid seal with the face of the wearer while providing a comfortable fit during long periods of wear. Such materials are available from various suppliers.

Filter body 228, flaps 230 and 232, and strips 270 and 272 are preferably designed to prevent or retard the passage of liquids from the exterior of mask 210 to the face of wearer 212. It is extremely difficult to construct a mask that will fit the facial configuration of all wearers without constructing the mask specifically for each individual face. The use of strips 270 and 272 along with flaps 230 and 232 greatly increases the different sizes and types of faces which can be effectively protected by mask 210. Forming flaps 230 and 232 from suitable resilient or stretchable material further improves facial fit with a large number of wearers.

Filter body 228 may comprise a plurality of pleats 233, 234 and 235 which allow expansion of filter body 228 to cover the mouth and nose of wearer 212. The number of pleats 233, 234 and 235 formed in filter body 228 may be varied to provide the desired fit with the face of wearer 212. Pleat 233 is preferably folded in a reverse direction as compared to pleats 234 and 235. By providing reverse pleat 233, filter body 228 has an increased tendency to stand away from the face of wearer 212.

For some applications filter body 228 may be formed without pleats. For other applications, filter body 228 may be formed with non-collapsing face panels such as shown in U.S. Pat. No. 4,606,341 entitled Non-Collapsible Surgical Face Mask. U.S. Pat. No. 4,606,341 is incorporated by reference for all purposes within this application. For still further applications, filter body 228 may be formed from only one layer of material or from multiple layers of material. Flaps 230 and 232 allow for a wide variety of options in selecting material with the desired breathability and fluid resistance for filter body 228.

The use of reverse pleat 233 in cooperation with pleats 234 and 235 forms a larger breathing chamber as compared to other soft, pleated style masks which contact a substantial portion of the wearer's face. The larger breathing chamber permits cooler and easier breathing associated with "off-the-face" style mask such as shown in U.S. Pat. No. 4,606,341. The present invention allows optimizing the volume of air contained within filter body 228 without sacrificing comfort to the wearer or filtration efficiency.

Strips of gasket-type sealing material 270 and 272 may be formed from the same types of thin film materials as previously described for strips 50, 52, 150 and 152. Various adhesives, ultrasonic seals and/or heat seals may be used to attach strips 270 and 272 on the interior of filter body 228 respectively adjacent to top edge 244 and bottom edge 246. A plurality of ultrasonic seals (sometimes referred to as ultrasonic welds) 244a and 246a have been found to be particularly advantageous for respectively attaching strips 270 and 272.

If the breathing chamber formed by filter body 228 is too large, excessive amounts of exhaled air may be retained within filter body 228 at normal breathing rates. By properly selecting the size of filter body 228 and flaps 230 and 232, excessive heating of air within filter body 228 is minimized and dizziness from prolonged periods of re-breathing exhaled air is also minimized. Since the present invention results in an enhanced fluid seal or barrier formed in part by strips 270 and 272 between the periphery of mask 210 and the face of wearer 212, incorporating the benefits of an "off-the-face" style face mask are important for extended periods of wearing mask 210.

As shown by the cutaway portion of FIG. 5, filter body 228 includes four layers of material with an external surface of cover stock 236 as the outermost layer. Inner layer or internal surface 238 which contacts the face of wearer 212 may be constructed of a light weight, highly porous, softened, non-irritating, non-woven fabric, such as Dexter, Inc. product No. 3768. Inner layer 238 is designed to prevent unwanted materials such as facial hair, loose fibers or perspiration from contacting intermediate layers 240 and 242 which might cause a wicking effect to draw liquids through filter body 228. Inner layer 238 also provides a comfortable surface for contact with the face of wearer 212.

Intermediate layer 240 preferably comprises a barrier material that is capable of differentiating between gases and liquids and may be, for example, Visqueen Film Products' low density polyethylene, Vispore X-6212. Non-wetting materials, such as used to form barrier material 240, have small apertures which prevent liquids with a relatively high surface tension from passing therethrough yet will allow gases with a low surface tension to pass therethrough. It is preferable to have the apertures as large as possible to allow easy breathing, and yet small enough to retard or prevent the flow of liquids. Intermediate layer 240 is designed to freely pass gases in either direction, while restricting the passage of liquids in at least on direction. Filter body 228 is constructed with barrier material 240 positioned to restrict liquid passage from the exterior of mask 210. Further description of the construction and operation of such barrier material may be found in U.S. Pat. No. 3,929,135 issued Dec. 230, 1975, to Thompson, assigned to Proctor and Gamble Co., and is incorporated by reference for all purposes.

The next intermediate layer is preferably filtration media 242, which may be, for example, melt blown polypropylene or polyester. Filtration media 242 is provided to inhibit the passage of airborne bacteria in either direction which will prevent passage of germs to and from wearer 212. Outermost layer 236 provides the external surface for filter body 228, which may be treated, for example, by spraying with a liquid repellant to render the external surface material resistant to liquids.

Outer layer 236 and filtration media layer 242 serve as an aid to barrier material 240 by slowing down any liquid that may be splashed, sprayed or thrown at mask 210. By requiring the liquid to pass through layers 236 and 242 prior to reaching barrier material 240, the liquid will have less pressure and barrier material 240 will be better able to prevent passage of the liquid. Outer layer 236 may be formed from non-woven material such as cellulose fiber.

Filter body 228 may be formed by bonding layers 236, 238, 240, and 242 with each other in a generally rectangular configuration. Such bonding is preferably provided along top edge 244, bottom edge 246 and lateral edges 250 and 252, respectively. The corresponding bonded areas 244a, 252a, 246a, and 250a may be formed by sewing, glue, heat sealing, welding, ultrasonic bonding and/or any other suitable bonding procedure.

Flaps 230 and 232 are preferably integrally attached to filter body 228 as part of the respective bonded areas 250a and 252a. Flaps 230 and 232 are preferably formed from fluid impervious material such as a plastic membrane and folded with a U-shaped configuration to form an opening to receive tie strips 216 and 218 therein. Bonded areas 220 and 222 are preferably used to secure the approximate mid-point of tie strips 216 and 218 with corresponding mid-points of flaps 230 and 232.

Top edge 244 of filter body 228 preferably includes an elongated malleable member 226 provided so that top edge 244 of filter body 228 can be configured to closely fit the contours of the nose and cheeks of wearer 212. Malleable member 248 is preferably constructed from an aluminum strip with a rectangular cross section, but may also be a molded or malleable steel or plastic member. Top edge 244, bottom edge 246 and flaps 230 and 232 cooperate with each other to define the periphery of mask 210 which contacts the face of wearer 212. Strips 270 and 272 along with flaps 230 and 232 substantially increase the area of contact with the face of wearer 212 as compared to a face mask having only tope edge 242, bottom edge 246 and lateral sides 250 and 252 in contact the face of wearer 212.

Typically surgical style pleated face masks have a generally rectangular or square configuration of approximately 7×7 inches prior to pleating. The length and width dimensions of a typical face mask may vary by ±½ inches resulting in a face mask which is often rectangular in configuration as compared to a square. For some applications, the present invention allows reducing the length of top edge 244 from 7 inches to as short as 4½ to 5 inches. Alternatively, the present invention allows increasing the length of top edge 244 as desired. Also, the distance from top edge 244 to bottom edge 246 when mask 210 has been placed over the face of wearer 212 may be reduced from 7 to 5½ to 6 inches. Therefore, flaps 230 and 232, along with other features of the present invention allow reducing the total area of the filter media associated with mask 210 from approximately 49 square inches to 25 square inches to 30 square inches while maintaining approximately the same effective area. This reduction in area results in a substantial savings in the cost of materials used to fabricate mask 210 while, at the same time, maintaining good breathability, high efficiency filtration, and providing an improved seal between the periphery of mask 210 and the face of wearer 212 by incorporating strips 270 and 272.

The arrangement of surgical ties 216 and 218 is such that portions 216a and 218a extending from top edge 244 may be placed over the top of the head of wearer 212. Portions 216b and 218b extending from bottom edge 246 may be positioned around the lower base of the head of wearer 212 as illustrated in FIG. 4. Positioning tie strips 216 and 218 in this manner results in compressing or gathering the respective flaps 230 and 232 to form a flat, flange type fluid barrier with the face of wearer 212. Also, securing surgical ties 216 and 218 in this manner urges strip 270 and 272 of gasket-type sealing material disposed respectively along top edge 244 and bottom edge 246 into fluid sealing engagement with the contours of the face of wearer 212. Surgical tie strips 216a, 218a, 216b and 218b may be positioned on the head of wearer 212 to provide the optimum full angle and the optimum amount of force to form the desired fluid barrier between the periphery of mask 210 and the face of wearer 212.

Top edge 244 with malleable member 248 conforms very closely to the configuration of the nose and cheeks of wearer 212. It is important that bottom edge 246 and the chin of wearer 212 and top edge 244 and the nose and cheeks of wearer 212 fit very closely since any leaks result in bypass or blow-by of fluids either entering mask 210 or being discharged from mask 210 during use by wearer 212.

For some applications, filter body 228 may include outer mask layer 236 that is preferably constructed from a spun-bonded polypropylene. Outer mask layer 236 may also be constructed from a bi-component and/or powder bonded material such as polyethylene or polypropylene, a cellulastic tissue, or a spun-bonded polyester. Outer mask layer 236 will typically have a basis weight range of 0.5 ounces per yard of 1.0 ounces per yard. 0.7 ounces per yard is one of the preferred basis weights for outer layers 236.

Inner mask layer 238 may alternatively comprise bicomponent polyethylene and polypropylene or bicomponent polyethylene and polyester. Layer 238 may also be constructed from polyester and/or polyethylene material or cellulastic tissue. Layer 238 will typically have a basis weight range of 0.4 ounce per yard to 0.75 ounces per yard. 0.413 ounces per yard is one of the preferred basis weights for layer 238. One or more intermediate layers of filter media may be disposed between outer mask layer 236 and inner mask layer 238. Selection of the number and type of intermediate layers of filter media will depend upon the intended use and function for mask 210. In FIG. 5, filter body 228 is shown with only two intermediate mask layers 240 and 242 which comprises the filter media for mask 210. These layers may be constructed from melt-blown polypropylene, extruded polycarbonate, melt-blown polyester, or melt-blown urethane.

Various types of material may be used for intermediate mask layers 240 and 242. For example, intermediate mask layer 240 may be formed from an expanded polytetrafluoroethylene (PTFE) membrane. Such materials are manufactured by W. L. Gore & Associates. A more complete description of the construction and operation of such materials can be found in U.S. Pat. No. 3,953,566 entitled Process for Producing Porous Products, issued on Apr. 27, 1976 to Robert W. Gore, and U.S. Pat. No. 4,187,390 entitled Porous Products for Process Therefor, issued on Feb. 5, 1980 to Richard W. Gore.

The present invention allows designing mask 210 with the optimum periphery to fit the face of wearer 212, the optimum dimensions for malleable strip 248 to form an enhanced fluid barrier with the nose and face of wearer 212. The present invention allows modification to the length of the top edge 244 and bottom edge 246 while maintaining the required surface area for efficient filtration and normal breathing through filter media 240.

The use of barrier materials which block the passage of liquids is particularly important when mask 212 is worn in an environment where wearer 212 may be exposed to "body fluids." These fluids such as blood, urine and saliva may contain highly contagious germs and viruses. Contact of AIDS-contaminated body fluids with another person's source of body fluids, such as the eyes, nose and mouth, may transmit the disease. Therefore, it is often preferable to include layer 240 and/or 242 which are resistant to the passage of liquids through filter body 228 to prevent body fluids from contacting the nose and mouth of wearer 212.

Various types of securing means may be used to attach a mask incorporating the present invention to the face of a wearer. Tie strips 216 and 218 shown in FIGS. 4–6 represent one of these alternative securing means. Also, elastic ear loops, such as shown in U.S. Pat. No. 4,802,473 entitled Face Mask with Ear Loops, may be satisfactorily used with the present invention. U.S. Pat. No. 4,802,473 is incorporated by reference for all purposes within this application. Tie strips 216 and 218 may be replaced by a continuous loop of resilient material which is disposed within but not bonded to flaps 230 and 232.

Surgical ties 216 and 218 may be formed from various types of material. For one application of the present invention surgical ties 216 and 218 are preferably formed from thermally bonded polypropylene having a basis weight of 1.5 to 1.65 ounces per square yard. This particular type of material can be ultrasonically welded, stitched or heat and pressure bonded in various patterns to provide a resilient securing means for use in attaching mask 210 to the face of wearer 212.

As shown in FIGS. 5 and 6, a single sonic stitch 224 is provided along the length of each surgical tie 216 and 218 to provide the desired longitudinal stretch and recovery capability. Single sonic stitch pattern 224 allows most of the material used to form surgical ties 216 and 218 to be open and free from the associated bonded area. Stitch pattern 224 allows surgical ties 216 and 218 to retain their naturally resilient characteristics.

By providing resilient surgical ties 216 and 218, the periphery of face mask 210 will maintain a tight fluid barrier with the face of wearer 212 over a relatively long period of time. Talking and other activities by wearer 212 will not compromise the integrity of the resulting fluid barrier. Laminated strips of material may also be used to form ties 216 and 218.

Figure 7:
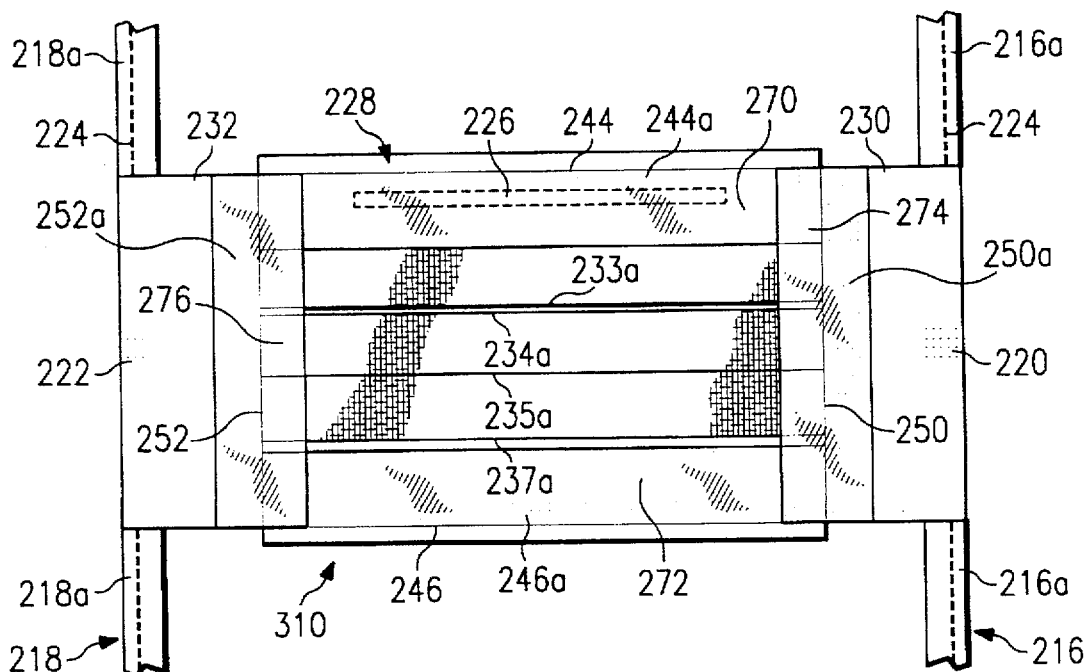
FIG. 7 is a back plan view of a face mask incorporating a further embodiment of the present invention.

Mask 310 incorporating still another embodiment of the present invention is shown in FIG. 7. Except for the addition of strips 274 and 276 of gasket-type sealing material, mask 310 is essentially the same as previously described mask 210. Strips 274 and 276 may be formed from the same gasket-type sealing material as strips 270 and 272. Strip 276 extends laterally along side 252 of filter body 228 between top edge 244 and bottom edge 246. In a similar manner, strip 276 extends laterally between top edge 244 and bottom edge 246 along side 250 of filter body 228. Only a portion of each strip 270, 272, 274 and 276 is preferably bonded with the interior of face mask 310 to provide flexibility between strips 270, 272, 274 and 276 and filter body 228. Strips 270, 272, 274 and 276 cooperate with each other to allow limited movement of filter body 224 during normal talking and/or breathing of wearer 212 without compromising the fluid barrier formed between the periphery of mask 310 and the face of wearer 212.

For some applications it may be desirable to apply suitable hydrogel-type materials and/or other biocompatible adhesive compounds to strips 50 and 52 for mask 10, strips 150 and 152 for mask 110 strips 270 and 272 for mask 210 and strips 270, 272, 274, and 276 for mask 310. For other applications strips 50, 52, 150, 152, 270, 272, and 274 and/or 276 may be eliminated from their respective face masks 10, 110, 210, and 310 and replaced by applying a layer of hydrogel or adhesive to the top edge, the bottom edge, and/or lateral rider of the respective face mask. For example, it may be desirable to apply hydrogel to lateral sides 250 and 252 on the interior surface of mask 210.

Examples of hydrogel type materials and compounds satisfactory for use with the present invention are shown in U.S. Pat. No. 5,306,504 entitled Skin Adhesive Hydrogel, Its Preparation and Uses; U.S. Pat. No. 5,254,338 entitled External Application Base or Auxiliary Agent and External Application Composition for Human Being or Animal Containing the Same; and U.S. Pat. No. 5,183,664 entitled Thin Film at EC Dressings, Preparation and Use. These three patents are representative of only a few of the many types of hydrogel materials and compounds which may be satisfactorily used with the present invention.

In addition to the previously discussed materials, face masks 10, 110, 210 and 310 may be manufactured using a wide variety of non-woven materials and/or microporous films. The teachings of the present invention allow incorporating new, state of the art materials into face masks 10, 110, 210 and 310.

Although the present invention has been described in detail with respect to alternative embodiments, various changes and modifications may be suggested to one skilled in the art, and it should be understood that various changes, substitutions, and alterations can be made hereto without departing from the spirit and scope of the invention as defined by the appended claims.

What is claimed is:

1. A disposable face mask comprising:

a filter body having an opening sized to cover the nose and mouth of a wearer, the body having top and bottom edges with the top edge arranged to extend across the nose of the wearer and the bottom edge arranged to extend under the chin of the wearer;

the top edge having ends opposite from each other and the bottom edge having ends opposite from each other;

first securing means attached to the filter body adjacent to each end of the top edge and arranged to extend generally about the back of the head of the wearer in an approximate linear continuation from the top edge, the first securing means for urging the top edge into tight engagement with the wearer to prevent fluid flow between the top edge and the wearer;

second securing means attached to the filter body adjacent to each end of the bottom edge and arranged to extend generally over the top of the head of the wearer in an approximate linear continuation from the bottom edge, the second securing means for urging the bottom edge into tight engagement with the wearer to prevent fluid flow between the bottom edge and the wearer;

a first strip of gasket-type sealing material disposed within the filter body adjacent to the opening and extending along the top edge;

the first securing means and the second securing means each having a respective first end and a second end with the first end of the first securing means and the first end of the second securing means disposed adjacent to each other and the second end of the first securing means and the second end of the second securing means disposed adjacent to each other;

a second strip of gasket-type sealing material disposed within the filter body adjacent to the opening and extending along the bottom edge; and the first sealing strip and the second sealing strip cooperating with each other to form a fluid barrier between the opening of the filter body and the face of the wearer.

2. The mask of claim 1 wherein the filter body further comprises:

an upper portion of generally trapezoidal configuration having a longer side forming the top edge;

a lower portion of generally trapezoidal configuration having a longer side forming the bottom edge; and the upper and lower portions of the filter body being joined along all remaining sides extending from the opening.

3. The mask of claim 1 further comprising the first strip of gasket-type sealing material and the second strip of gasket-type sealing material formed from a thin film layer of plastic type material and bonded respectively with the top edge and the bottom edge of the opening in the filter body.

4. The mask of claim 1 further comprising:

a portion of the first strip of gasket-type sealing material extending from the opening of the filter body; and a portion of the second strip of gasket-type sealing material extending from the opening of the filter body.

5. The mask of claim 1 wherein the filter body further comprises an intermediate layer of material which is gas permeable in both directions through the filter body and liquid impermeable in the direction from outside the filter body to inside the filter body.

6. The mask of claim 1 wherein the filter body further comprises an intermediate layer of filter media formed from expanded polytetrafluoroethylene (PTFE).

7. The mask of claim 6 wherein the filter body further comprises a first layer of bicomponent material disposed on one side of the intermediate layer of expanded polytetrafluoroethylene and a second layer of the same bicomponent material disposed on the opposite side of the layer of expanded polytetrafluoroethylene.

8. A disposable face mask comprising:

a filter body sized to fit over the mouth and nose of a wearer, the filter body having top and bottom edges with the top edge arranged to extend across the nose and cheeks of the wearer and the bottom edge arranged to extend under the chin of the wearer;

the filter body having a pair of lateral edges extending between the top edge and the bottom edge;

a first strip of sealing material disposed on the interior of the filter body adjacent to and extending along the top edge;

a second strip of sealing material disposed on the interior of the filter body adjacent to and extending along the bottom edge;

a separate flap of different material from the filter body attached to each lateral edge of the filter body and arranged to extend from the filter body;

first securing means and second securing means attached to the respective flaps and arranged to extend generally about the head of the wearer, the first and second securing means cooperating with the flaps for urging the first strip of sealing material on the top edge and the second strip of sealing material on the bottom edge into tight engagement with the wearer to prevent undesired fluid flow between the top edge and the bottom edge and the wearer's face; and the flaps cooperating with their respective first securing means and second securing means to prevent undesired fluid flow between the respective lateral edges of the filter body and the face of the wearer.

9. The mask of claim 8 wherein the first strip of sealing material and the second strip of sealing material further comprise a thin layer of plastic film bonded respectively with the top edge and the bottom edge of the filter body with a portion of the first strip of material and a portion of the second strip of sealing material extending respectively from the top edge and the bottom edge of the filter body.

10. The mask of claim 8 further comprising an elongated malleable member located in the top edge for conforming the top edge to the contours of the wearer's nose and cheeks.

11. The mask of claim 8 wherein the first strip of sealing material and the second strip of sealing material comprises hydrogel.

12. The mask of claim 8 wherein the filter body comprises a layer of filter media for restricting the flow of liquids through the filter body.

13. The mask of claim 8 wherein the filter body further comprises an intermediate layer of filter media formed from expanded polytetrafluoroethylene (PTFE).

14. The mask of claim 8 wherein the filter body further comprises a first layer of bicomponent material disposed on one side of the intermediate layer of expanded polytetrafluoroethylene and a second layer of the same bicomponent material disposed on the opposite side of the layer of expanded polytetrafluoroethylene.

15. A disposable face mask comprising:

a filter body having an opening sized to cover the nose and mouth of a wearer, the filter body having top and bottom edges with the top edge arranged to extend across the nose and cheeks of the wearer, and the bottom edge arranged to extend under the chin of the wearer;

the filter comprising an upper portion of generally trapezoidal configuration having a longer side forming the top edge and a lower portion of generally trapezoidal configuration having a longer side forming the bottom edge;

the longer side of the top edge and the longer side of the bottom edge having generally matching dimensions and defining in part the opening of the filter body;

the body and lower portions being joined along all remaining sides; and the filter body having a shorter side opposite from the longer side and generally parallel with the longer side, and the length of the longer side approximately three times the length of the shorter side.

16. The mask of claim 15 wherein the filter body further comprises:

the dimensions of the upper portion corresponding to the dimensions of the lower portion; and the distance from the longer side to the shorter side approximately equal to the length of the shorter side.

17. A disposable face mask comprising:

a filter body having an opening sized to cover the nose and mouth of a wearer, the filter body having top and bottom edges with the top edge arranged to extend across the nose and cheeks of the wearer, and the bottom edge arranged to extend under the chin of the wearer;

the filter body comprising an upper portion of generally trapezoidal configuration having a longer side forming the top edge and a lower portion of generally trapezoidal configuration having a longer side forming the bottom edge;

the longer side of the top edge and the longer side of the bottom edge having generally matching dimensions and defining in part the opening of the filter body;

the upper and lower portions of the filter body being joined along all remaining sides;

the filter body having a shorter side opposite from the longer side and generally parallel with the longer side and the length of the longer side approximately three times the length of the shorter side;

a first strip of sealing material disposed within the filter body adjacent to the opening and extending along the top edge;

a second strip of sealing material disposed within the filter body adjacent to the opening and extending along the bottom edge; and the first sealing strip and the second sealing strip cooperating with each other to form a fluid barrier between the opening of the filter body and the face of the wearer.

18. The mask of claim 17 wherein the filter body further comprises:

the dimensions of the upper portion corresponding to the dimensions of the lower portion; and the distance from the longer side to the shorter side approximately equal to the length of the shorter side.

19. The mask of claim 17 wherein the filter body further comprises an intermediate layer of material which is gas permeable in both directions through the filter body and liquid impermeable in the direction from outside the filter body to inside the filter body.

20. The mask of claim 17 wherein the first strip of sealing material and the second strip of sealing material further comprises hydrogel.

21. The mask of claim 17, further comprising:

the first strip of sealing material extending partially from the opening of the filter body; and the second strip of sealing material extending partially from the opening of the filter body.

22. A disposable face mask comprising:

a filter body having an opening sized to cover the nose and the mouth of a wearer, the body having top and bottom edges with the top edge arranged to extend across the nose of the wearer and the bottom edge arranged to extend under the chin of the wearer;

the top edge having ends opposite from each other and the bottom edge having ends opposite from each other with at least three edges of the filter body extending from the top edge and the bottom edge;

first securing means attached to the filter body adjacent to each end of the top edge and arranged to extend generally about the back of the head of the wearer in an approximate linear continuation of the top edge, the first securing means for urging the top edge into tight engagement with the wearer for preventing fluid flow between the top edge and the wearer;

second securing means attached to the filter body adjacent to each end of the bottom edge and arranged to extend generally over the top of the wearer's head in an approximate linear continuation of the bottom edge, the second securing means for urging the bottom edge in tight engagement with the wearer for preventing fluid flow between the bottom edge and the wearer;

the first securing means and the second securing means each having a respective first end and a second end with the first end of the first securing means and the first end of the second securing means disposed adjacent to each other and the second end of the first securing means and the second end of the second securing means disposed adjacent to each other;

a bonded border formed along the at least three edges of the filter body with the bonded border forming in part at least three closed sides of the filter body extending from the opening;

a first strip of material disposed within the filter body adjacent to the opening and extending alone the top edge to form a fluid seal with the face of the wearer; and a second strip of material disposed within the filter body adjacent to the opening and extending alone the bottom edge to form a fluid seal with the face of the wearer.

23. The mask of claim 22 wherein the bonded border further comprises a width of approximately ¼ inches.

24. The mask of claim 22, further comprising:

the first strip of sealing material extending partially from the opening of the filter body; and the second strip of sealing material extending partially from the opening of the filter body.

25. A disposable face mask comprising:

a filter body sized to fit over the mouth and nose of a wearer, the filter body having top and bottom edges with the top edge arranged to extend across the nose and cheeks of the wearer and the bottom edge arranged to extend under the chin of the wearer;

the filter body having a pair of lateral edges extending between the top edge and the bottom edge;

a separate flap attached to each lateral edge of the filter body and arranged to extend from the filter body;

the flaps formed from fluid impervious, resilient material which is different from the material used to form the filter body;

first securing means and second securing means attached to respective flaps and arranged to extend generally about the head of the wearer, the first and second securing means cooperating with the respective flaps for urging the top edge and the bottom edge into tight engagement with the face of the wearer to prevent undesired fluid flow between the top edge and the bottom edge and the wearer's face;

the flaps cooperating with their respective first securing means and second securing means to prevent undesired fluid flow between the respective sides of the filter body and the face of the wearer;

a first strip of material disposed within the filter body adjacent to and extending along the top edge for forming a fluid seal with the face of the wearer; and a second strip of material disposed within the filter body adjacent to and mending along the bottom edge for forming a fluid seal with the face of the wearer.

26. The mask of claim 25, further comprising:

the first strip of sealing material extending partially from the top edge of the filter body; and the second stop of sealing material extending partially from the bottom edge of the filter body.

27. The mask of claim 25 further comprising the first strip of sealing material and the second strip of sealing material selected from the group consisting of thin plastic film, hydrogel, polyethylene and polypropylene.

* * * * *